US012364511B2

(12) United States Patent  
Ensign et al.

(10) Patent No.: US 12,364,511 B2  
(45) Date of Patent: *Jul. 22, 2025

(54) PRESS-ON PEDICLE SCREW ASSEMBLY

(71) Applicant: Nexus Spine, L.L.C., Salt Lake City, UT (US)

(72) Inventors: Michael D. Ensign, Salt Lake City, UT (US); David T. Hawkes, Pleasant Grove, UT (US)

(73) Assignee: NEXUS SPINE, LLC, Salt Lake City, UT (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/532,256

(22) Filed: Aug. 5, 2019

(65) Prior Publication Data

US 2024/0415546 A1 Dec. 19, 2024

Related U.S. Application Data

(63) Continuation of application No. 15/871,973, filed on Jan. 15, 2018, now Pat. No. 10,368,915, which is a (Continued)

(51) Int. Cl.  
*A61B 17/70* (2006.01)

(52) U.S. Cl.  
CPC ...... *A61B 17/7007* (2013.01); *A61B 17/7035* (2013.01)

(58) Field of Classification Search  
CPC ............ A61B 17/7002; A61B 17/7004; A61B 17/7007; A61B 17/7032; A61B 17/7034; A61B 17/7035; A61B 17/7043

(Continued)

(56) References Cited

U.S. PATENT DOCUMENTS 3,945,053 A 3/1976 Hillberry et al.  
4,445,635 A 5/1984 Barr  
(Continued)

FOREIGN PATENT DOCUMENTS

EP 1072228 A1 1/2001  
EP 1224915 A1 7/2002  
(Continued)

OTHER PUBLICATIONS

Jeanneau et al.;"A Compliant Rolling Contact Joint and it's Application in a 3-DOF Planar Parallel Mechanism with Kinematic Analysis"; Proceedings ofDETC'04, ASME 2004 Design Engineering Technical Conferences and Computers and Information in Engineering Conference; Sep. 28-Oct. 2, 2004; Salt Lake City, Utah USA DETC2004-57264, 2004 by ASME.

(Continued)

*Primary Examiner* — Eduardo C Robert  
*Assistant Examiner* — Christina Negrellirodriguez  
(74) *Attorney, Agent, or Firm* — Bryant J. Keller; John Oldroyd; Kirton McConkie

(57) ABSTRACT

A tulip assembly configured to be coupled to a screw head having a first diameter includes a housing, wherein the housing defines an inner diameter configured to engage the first diameter of the screw head. The exemplary inner diameter of the housing being smaller than the first diameter of the screw head.

20 Claims, 10 Drawing Sheets

Related U.S. Application Data continuation of application No. 11/952,709, filed on Dec. 7, 2007, now Pat. No. 9,867,640.

(60) Provisional application No. 60/873,698, filed on Dec. 7, 2006.

(58) Field of Classification Search
USPC ................ 606/246–253, 264–279, 300–321
See application file for complete search history.

(56) References Cited

U.S. PATENT DOCUMENTS

| | | | |
|---|---|---|---|
| 5,405,408 A | 4/1995 | Pitkin | |
| 5,415,661 A | 5/1995 | Holmes | |
| 5,733,285 A | 3/1998 | Errico et al. | |
| 5,772,661 A | 6/1998 | Michelson | |
| 5,964,760 A | 10/1999 | Richelsoph | |
| 6,045,552 A | 4/2000 | Zucherman et al. | |
| 6,063,089 A | 5/2000 | Errico et al. | |
| 6,355,040 B1 | 3/2002 | Richelsoph et al. | |
| 6,379,354 B1 | 4/2002 | Rogozinski | |
| 6,440,169 B1 | 8/2002 | Elberg et al. | |
| 6,527,804 B1 | 3/2003 | Gauchet et al. | |
| 6,540,785 B1 | 4/2003 | Gill et al. | |
| 6,572,653 B1 | 6/2003 | Simonson | |
| 6,579,320 B1 | 6/2003 | Gauchet et al. | |
| 6,610,093 B1 | 8/2003 | Pisharodi | |
| 6,626,904 B1 | 9/2003 | Jammet et al. | |
| 6,645,248 B2 | 11/2003 | Casutt | |
| 6,723,127 B2 | 4/2004 | Ralph et al. | |
| 6,793,678 B2 | 9/2004 | Hawkins | |
| 6,802,867 B2 | 10/2004 | Manasas et al. | |
| 6,811,567 B2 | 11/2004 | Reiley | |
| 6,863,688 B2 | 3/2005 | Ralph et al. | |
| 6,869,433 B2 | 3/2005 | Glasscott | |
| 6,936,071 B1 | 8/2005 | Marnay et al. | |
| 6,949,123 B2 | 9/2005 | Reiley | |
| 6,964,666 B2 | 11/2005 | Jackson | |
| 6,966,910 B2 | 11/2005 | Ritland | |
| 6,974,478 B2 | 12/2005 | Reiley et al. | |
| 6,991,632 B2 | 1/2006 | Ritland | |
| 6,997,955 B2 | 2/2006 | Zubok et al. | |
| 7,029,475 B2 | 4/2006 | Panjabi | |
| 7,074,238 B2 | 7/2006 | Stinson et al. | |
| 7,115,129 B2 | 10/2006 | Heggeness | |
| 7,144,396 B2 | 12/2006 | Shluzas | |
| 7,207,992 B2 | 4/2007 | Ritland | |
| 7,229,441 B2 | 6/2007 | Trieu et al. | |
| 7,322,982 B2 | 1/2008 | Vincent-Prestigiacomo | |
| 7,326,210 B2 | 2/2008 | Jahng et al. | |
| 7,361,196 B2 | 4/2008 | Fallin et al. | |
| 7,371,238 B2 | 5/2008 | Soboleski et al. | |
| 7,377,942 B2 | 5/2008 | Berry | |
| 7,445,627 B2 | 11/2008 | Hawkes et al. | |
| 7,445,635 B2 | 11/2008 | Fallin et al. | |
| 7,458,981 B2 | 12/2008 | Fielding et al. | |
| 7,476,238 B2 | 1/2009 | Panjabi | |
| 7,476,251 B2 | 1/2009 | Zucherman et al. | |
| 7,481,830 B2 | 1/2009 | Wall et al. | |
| 7,485,133 B2 | 2/2009 | Cannon et al. | |
| 7,485,134 B2 | 2/2009 | Simonson | |
| 7,485,146 B1 | 2/2009 | Crook et al. | |
| 7,491,218 B2 | 2/2009 | Landry et al. | |
| 7,491,238 B2 | 2/2009 | Arnin et al. | |
| 7,491,240 B1 | 2/2009 | Carver et al. | |
| 7,494,507 B2 | 2/2009 | Dixon et al. | |
| 7,537,615 B2 | 5/2009 | Lemaire | |
| 7,618,441 B2 | 11/2009 | Groiso | |
| 7,632,292 B2 | 12/2009 | Sengupta et al. | |
| 7,682,375 B2 | 3/2010 | Ritland | |
| 7,785,351 B2 | 8/2010 | Gordon et al. | |
| 7,909,877 B2 | 3/2011 | Krueger et al. | |
| 9,157,497 B1 | 10/2015 | Magleby et al. | |
| 9,232,965 B2 | 1/2016 | Hawkes | |
| 9,867,640 B2 | 1/2018 | Ensign et al. | |
| 10,368,915 B2* | 8/2019 | Ensign | A61B 17/7001 |
| 2002/0138077 A1 | 9/2002 | Ferree | |
| 2002/0151900 A1 | 10/2002 | Glasscott | |
| 2003/0171751 A1 | 9/2003 | Ritland | |
| 2004/0002708 A1 | 1/2004 | Ritland | |
| 2004/0176849 A1 | 9/2004 | Zubok et al. | |
| 2005/0038432 A1 | 2/2005 | Shaolian et al. | |
| 2005/0101954 A1 | 5/2005 | Simonson | |
| 2005/0113927 A1 | 5/2005 | Malek | |
| 2005/0125065 A1 | 6/2005 | Zucherman et al. | |
| 2005/0149023 A1 | 7/2005 | Ritland | |
| 2005/0159818 A1 | 7/2005 | Blain | |
| 2005/0165487 A1 | 7/2005 | Muhanna et al. | |
| 2005/0177156 A1 | 8/2005 | Timm et al. | |
| 2005/0192573 A1 | 9/2005 | Abdelgany et al. | |
| 2005/0203516 A1 | 9/2005 | Biedermann et al. | |
| 2005/0228382 A1 | 10/2005 | Richelsoph et al. | |
| 2005/0240270 A1 | 10/2005 | Zubok et al. | |
| 2005/0261772 A1 | 11/2005 | Filippi et al. | |
| 2006/0009768 A1 | 1/2006 | Ritland | |
| 2006/0009850 A1 | 1/2006 | Frigg et al. | |
| 2006/0025770 A1 | 2/2006 | Schlapfer et al. | |
| 2006/0036240 A1 | 2/2006 | Colleran et al. | |
| 2006/0041314 A1 | 2/2006 | Millard | |
| 2006/0052784 A1 | 3/2006 | Dant et al. | |
| 2006/0074419 A1 | 4/2006 | Taylor et al. | |
| 2006/0084987 A1 | 4/2006 | Kim | |
| 2006/0173456 A1* | 8/2006 | Hawkes | A61B 17/7037 606/264 |
| 2006/0189983 A1 | 8/2006 | Fallin et al. | |
| 2006/0190079 A1 | 8/2006 | Istephanous et al. | |
| 2006/0217712 A1 | 9/2006 | Mueller et al. | |
| 2006/0229609 A1 | 10/2006 | Wang | |
| 2006/0240533 A1 | 10/2006 | Sengupta et al. | |
| 2006/0271047 A1 | 11/2006 | Jackson | |
| 2006/0271051 A1 | 11/2006 | Berrevoets et al. | |
| 2007/0016193 A1 | 1/2007 | Ritland | |
| 2007/0043365 A1 | 2/2007 | Ritland | |
| 2007/0049936 A1 | 3/2007 | Colleran et al. | |
| 2007/0088440 A1 | 4/2007 | Eisermann et al. | |
| 2007/0093819 A1 | 4/2007 | Albert | |
| 2007/0179618 A1 | 8/2007 | Trieu et al. | |
| 2008/0015588 A1 | 1/2008 | Hawkes | |
| 2008/0077246 A1 | 3/2008 | Fehling et al. | |
| 2008/0140075 A1 | 6/2008 | Ensign et al. | |
| 2008/0154308 A1 | 6/2008 | Sherman et al. | |
| 2008/0167688 A1 | 7/2008 | Fauth et al. | |
| 2008/0183209 A1 | 7/2008 | Robinson et al. | |
| 2008/0195208 A1 | 8/2008 | Castellvi et al. | |
| 2008/0195213 A1 | 8/2008 | Halverson et al. | |
| 2008/0234739 A1 | 9/2008 | Hudgins et al. | |
| 2008/0312693 A1 | 12/2008 | Trautwein et al. | |
| 2009/0005819 A1 | 1/2009 | Ben-Mokhtar et al. | |
| 2009/0048631 A1 | 2/2009 | Bhatnagar et al. | |
| 2009/0228045 A1 | 9/2009 | Hayes et al. | |
| 2009/0259257 A1 | 10/2009 | Prevost | |
| 2009/0270921 A1 | 10/2009 | Krause | |
| 2010/0204732 A1 | 8/2010 | Aschmann et al. | |
| 2010/0211106 A1 | 8/2010 | Bowden et al. | |
| 2010/0217324 A1 | 8/2010 | Bowden et al. | |
| 2010/0217326 A1 | 8/2010 | Bowden et al. | |
| 2010/0217334 A1 | 8/2010 | Hawkes | |
| 2010/0222821 A1 | 9/2010 | Bowden et al. | |
| 2010/0222823 A1 | 9/2010 | Bowden et al. | |
| 2010/0241232 A1 | 9/2010 | Halverson et al. | |

FOREIGN PATENT DOCUMENTS

| | | |
|---|---|---|
| EP | 1970031 A2 | 9/2008 |
| KR | 1020050080493 A | 8/2005 |
| KR | 1020060113318 A | 11/2006 |
| WO | 6355040 B1 | 3/2002 |
| WO | 2004071344 A2 | 8/2004 |
| WO | 2005051243 A2 | 6/2005 |
| WO | 2005107654 A1 | 11/2005 |
| WO | 2006127992 A2 | 11/2006 |
| WO | 2007041265 A1 | 4/2007 |
| WO | 2008070840 A1 | 6/2008 |
| WO | 2008100891 A1 | 8/2008 |

(56) References Cited

FOREIGN PATENT DOCUMENTS

| WO | 2010030906 A1 | 3/2010 |
|---|---|---|
| WO | 2010096621 A2 | 8/2010 |
| WO | 2010096829 A2 | 8/2010 |
| WO | 2010108010 A2 | 9/2010 |
| WO | 2012177412 A2 | 12/2012 |

OTHER PUBLICATIONS

Cannon et al.; "Compliant Rolling-Contact Element Mechanisms"; Proceedings of IDETC/CIE 2005, 2005 ASME Design Engineering Technical Conferences & Computers and Information in Engineering Conference, Sep. 24-28, 2005, 2005; Long Beach, California, USA; DETC2005-84073.

Halverson et al.; "Concepts for Achieving Multi-Stability in Compliant Rolling-Contact Elements"; Proceedings of IDETC/CIE 2007; ASME 2007 International Design Engineering Technical Conferences & Computers and Information in Engineering Conference; Sep. 24-28, 2007; Las Vegas, USA; DETC2007-34836.

Halverson et al.; Tension-Based Multi-Stable Compliant Rolling-Contact Elements: 13th National Conference on Mechanisms and Machines (NaCoMM-2007); IISc, Bangalore, India; Dec. 12-13, 2007.

Jacobsen et al.; "Components for the design of Lamina Emergent Mechanism"; Proceedings of IMECE 2007, 2007 ASME International Mechanical Engineering Congress and Exposition; Nov. 10-16, 2007; Seattle, USA.

Jacobsen et al.; "Mechanism and Machine Theory"; Mechanism and Machine Theory; 2009; pp. 2098-2109; vol. 44; Elsevier.

Stratton et al.; Force-Displacement Model of the Flexsure™ Spinal Implant; Proceedings of the ASME 2010 International Design Engineering Technical Conferences and Computers and Information in Engineering Conference IDETC/CIE 2010; Aug. 15-18; Montreal, Quebec, Canada.

\* cited by examiner

PRESS-ON PEDICLE SCREW ASSEMBLY

CROSS-REFERENCE TO RELATED APPLICATIONS

This application is a continuation of U.S. patent application Ser. No. 15/871,973 filed Jan. 15, 2018, which is a continuation of U.S. patent application Ser. No. 11/952,709 filed Dec. 7, 2007, now U.S. Pat. No. 9,867,640 issued Jan. 16, 2018, which claims the benefit under 35 U.S.C. § 119 (e) of U.S. Provisional Patent Application No. 60/873,698, filed Dec. 7, 2006, titled "Press on Screw Tulip," which applications are incorporated herein by reference in their entirety.

TECHNICAL FIELD

1. Field of the Invention

The present exemplary system and method relates to medical devices. More particularly, the present exemplary system and method relates to percutaneous orthopedic rod placement devices.

2. BACKGROUND AND RELATED ART

The use of bone stabilization/fixation devices to align or position bones is well established. Furthermore, the use of spinal bone stabilization/fixation devices to align or position specific vertebrae or a region of the spine is well established. Typically such devices for the spine utilize a spinal fixation element, comprised of a relatively rigid member such as a plate or a rod that is used as a coupler between adjacent vertebrae. Such a spinal fixation element can effect a rigid positioning of adjacent vertebrae when attached to the pedicle portion of the vertebrae using pedicle bone anchorage screws. Once the coupled vertebrae are spatially fixed in position, procedures can be performed, healing can proceed, or spinal fusion may take place.

Spinal fixation elements may be introduced to stabilize the various vertebrae of the spine. Some devices for this purpose are designed to be attached directly to the spine, but the generally invasive nature of standard paraspinal approach used to implant these devices may pose drawbacks. For example, muscle disruption and blood loss may result from standard paraspinal implantation approaches.

Conventional pedicle screw systems and even more recently designed pedicle screw systems also have several drawbacks. Some of these pedicle screw systems are rather large and bulky, which may result in more tissue damage in and around the surgical site when the pedicle screw system is installed during surgery. The prior art pedicle screw systems have a rod-receiving device that is pre-operatively coupled or attached to the pedicle screw. In addition, some of the prior art pedicle screw systems include numerous components that must all be carefully assembled together. Further, traditional pedicle screw systems are pre-operatively assembled, which makes these systems more difficult to install and maneuver in a spinal operation where MIS techniques are used.

BRIEF SUMMARY OF THE INVENTION

A tulip assembly configured to be coupled to a screw head having a first diameter includes a housing, wherein the housing defines an inner diameter configured to engage the first diameter of the screw head. The exemplary inner diameter of the housing being smaller than the first diameter of the screw head.

BRIEF DESCRIPTION OF THE DRAWINGS

The accompanying drawings illustrate various embodiments of the present system and method and are a part of the specification. Together with the following description, the drawings demonstrate and explain the principles of the present system and method. The illustrated embodiments are examples of the present system and method and do not limit the scope thereof.

Throughout the drawings, identical reference numbers designate similar but not necessarily identical elements.

DETAILED DESCRIPTION OF THE INVENTION

Figure 1:
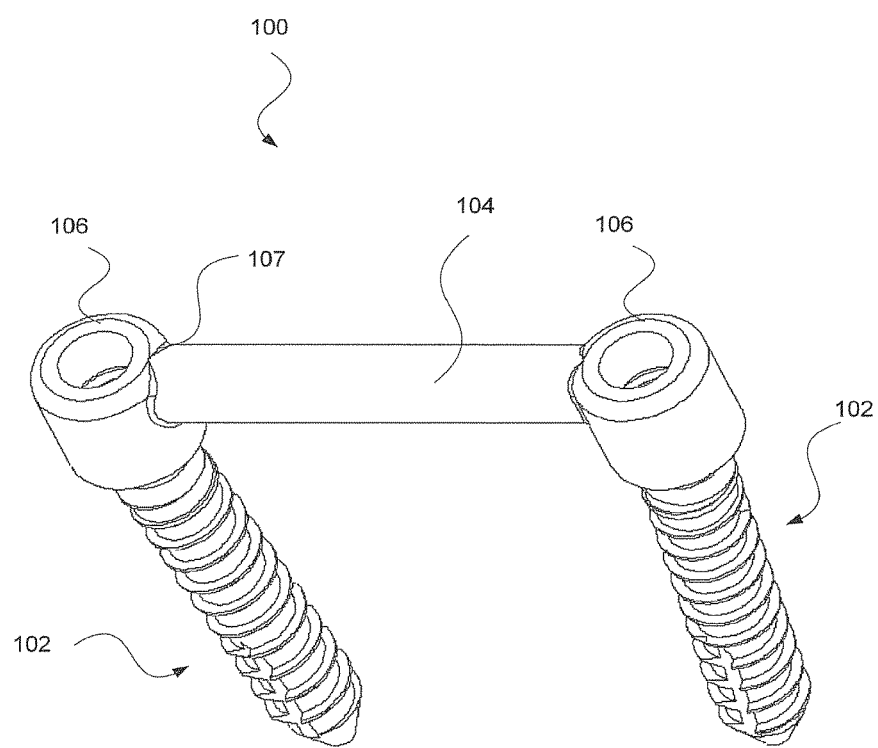
FIG. 1 is an assembled perspective view of a press-on pedicle screw system, according to one exemplary embodiment.

The present specification describes a system and a method for securely coupling a tulip assembly relative to a pedicle screw via an interference fit. Further, according to one exemplary embodiment, the present specification describes the structure of a tulip assembly configured to be placed on the head of a pedicle screw after placement of the pedicle screw in a patient's body and configured to receive and positionally secure a top loaded rod. Further details of the present exemplary system and method will be provided below.

By way of example, pedicle screw systems may be fixed in the spine in a posterior lumbar fusion process via minimally invasive surgery (MIS) techniques. The systems are inserted into the pedicles of the spine and then interconnected with rods to manipulate (e.g., correct the curvature, compress or expand, and/or structurally reinforce) at least portions of the spine. Using the MIS approach to spinal fixation and/or correction surgery has been shown to decrease a patient's recovery time and reduce the risks of follow-up surgeries.

The ability to efficiently perform spinal fixation and/or correction surgeries using MIS techniques is enhanced by the use of pedicle screw systems provided in accordance with the present exemplary systems and methods, which systems and methods provide a number of advantages over conventional systems. For example, a pedicle screw system in accordance with one embodiment of the present exemplary system and method provides the advantage that the pedicle screw may be inserted into the bone without being pre-operatively coupled with the rod-coupling assembly (hereinafter referred to as a tulip assembly). This is advantageous because the surgeon often needs to do other inter-body work after inserting the pedicle screw, but before attaching the tulip assembly. Such an advantageous pedicle screw system may be even more crucial when using MIS techniques because the inter-body spatial boundaries in which the surgeon must work may be quite limited.

In addition, pedicle screw systems in accordance with several embodiments of the present system and method advantageously reduce the overall size and height of the pedicle screw system when compared to traditional pedicle screw systems. Reduced size and height of the pedicle screw system reduces tissue damage surrounding a surgical site and may also increase a patient's relative comfort.

The term "distraction," when used herein and when used in a medical sense, generally relates to joint surfaces and suggests that the joint surfaces move perpendicular to one another. However when "traction" and/or "distraction" is performed, for example on spinal sections, the spinal sections may move relative to one another through a combination of distraction and gliding, and/or other degrees of freedom.

Another advantageous feature of at least one embodiment of the present exemplary system and method is that an all-inclusive tulip assembly that can be coupled to the head portion of the pedicle screw intra-operatively is disclosed. This advantageous tulip assembly may include the aspects or features that enable the tulip assembly to be locked onto the head portion of the pedicle screw. The present exemplary tulip assembly may decrease the complexity of the pedicle screw system installation while simultaneously reducing the overall size of the pedicle screw system.

In the following description, for purposes of explanation, numerous specific details are set forth in order to provide a thorough understanding of the present system and method for providing a press-on screw assembly configured to be coupled to the head of a spinal fastener via a compression fit. It will be apparent, however, to one skilled in the art that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Overall Structure

While the present system and method may be practiced by any number of bone fixation systems, a first exemplary embodiment of the present system and method will be described herein, for ease of explanation only, in the context of a pedicle screw system. Accordingly, the present system and method includes, according to one exemplary embodiment illustrated in FIG. 1, a pedicle screw system (100) including a pedicle screw (102), a rod member (104), and at least one coupling assemblies (106), herein after referred to as a tulip assembly (106). According to one exemplary embodiment of the present system and method, the tulip assembly (106) is configured to receive and securely position the rod member (104). Alternatively, as illustrated in FIG. 1, the at least one tulip assembly (106) may be securely and permanently coupled to the rod member (104) at a coupling site (107) via any number of coupling means, as will be described in detail below. According to the present exemplary system and method, the at least one tulip assembly (106) is configured to be securely coupled to the pedicle screw (102) via an interference fit. Operation of the tulip assembly (106) as well as its interaction with both the pedicle screw (102) and the rod (104) will be described in further detail below with reference to the Figures.

According to one exemplary embodiment, FIG. 1 generally shows a pedicle screw system (100) comprising a pedicle screw (102), a rod member (104), and a coupling assembly (106), hereinafter referred to as a tulip assembly (106). As illustrated in FIG. 1, the pedicle screw system (100) is configured to securely couple the tulip assembly (106) to the pedicle screw (102), thereby locking or fixing the tulip assembly (106) in a relative angular position relative to the pedicle screw (102). Additionally, as shown in FIG. 1, the present exemplary pedicle screw system (100) is devoid of separate pedicle screw coupling features and therefore is configured to couple the head of a pedicle screw while minimizing the outer diameter size of the tulip assembly (106).

Figure 2:
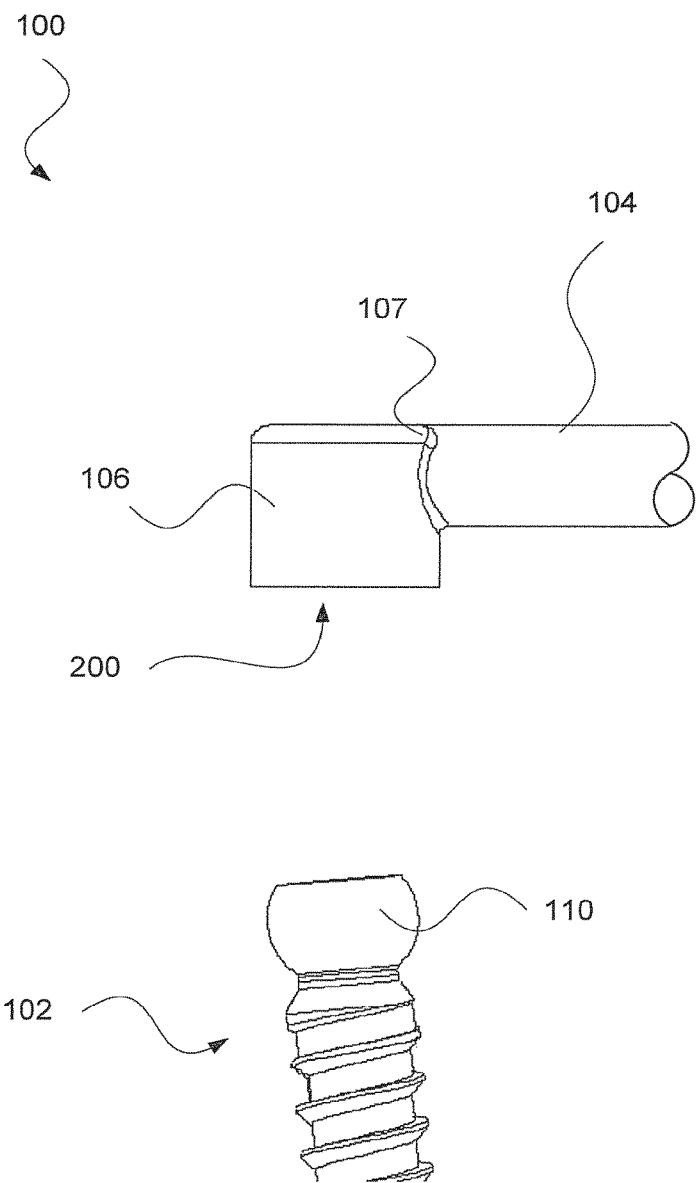
FIG. 2 is a partial side unassembled view of a press-on pedicle screw system, according to one exemplary embodiment.

FIG. 2 illustrates an unassembled exploded side view of the present pedicle screw system (100), according to one exemplary embodiment. As illustrated in FIG. 2, the coupling assembly or tulip assembly (106) of the pedicle screw system (100) includes an engagement orifice (200) configured to engage the head portion (110) of the pedicle screw (102), as described in further detail below. Detailed descriptions of each component of the present pedicle screw system (100), along with a number of alternative embodiments will be described in further detail below, with reference to FIGS. 2 through 9.

Figure 3:
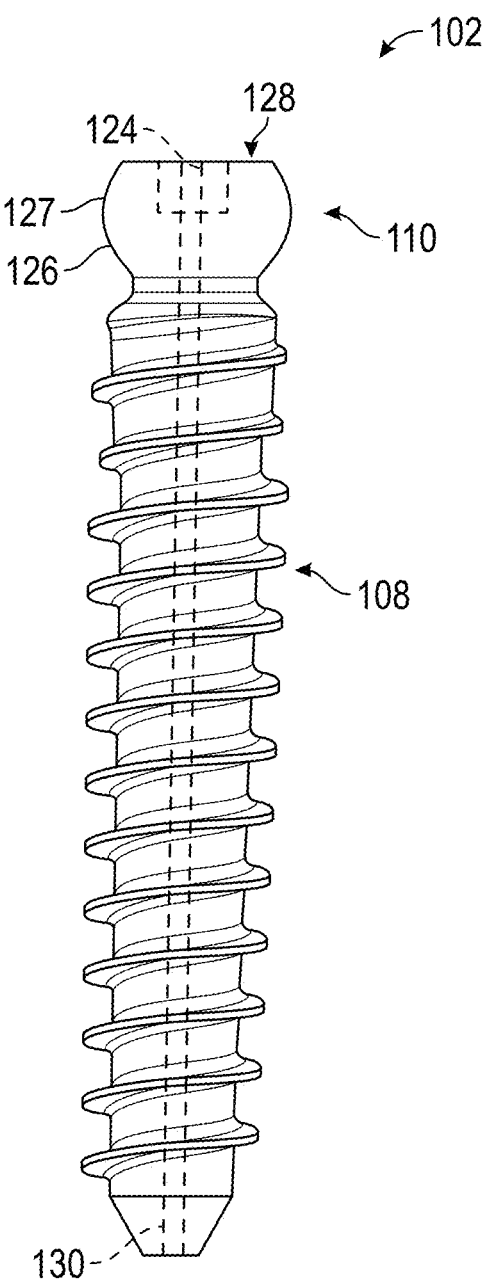
FIG. 3 is a side view of a pedicle screw, according to one exemplary embodiment.

FIG. 3 further illustrates the components of a pedicle screw (102) that may be used in connection with the present exemplary system and method, according to one exemplary embodiment. As illustrated in FIG. 3, the pedicle screw (102) includes an elongated, threaded portion (108) and a head portion (110). Although pedicle screws (102) are generally known in the art, the head portions (110) may be of varying configurations depending on what type of tulip assembly (160) is to be coupled to the pedicle screw (102). The head portion (110) of the present exemplary pedicle screw (102) includes a driving feature (124) and a maximum diameter portion (126). The driving feature (124) of the present exemplary pedicle screw (102) permits the screw to be inserted into a pedicle bone and/or other bone. According to one exemplary embodiment, the pedicle bone is a part of a vertebra that connects the lamina with a vertebral body. Additionally, according to the present exemplary embodiment, the driving feature (124) can be used to adjust the pedicle screw (102) prior to or after the tulip assembly (106) is coupled to the pedicle screw (102). In the illustrated embodiment, the head portion (110) of the pedicle screw (102) is coupled to the threaded portion (108) and includes a generally spherical surface (127) with a truncated or flat top surface (128).

In one exemplary embodiment, the pedicle screw (102) is cannulated, which means a channel (130) (shown in dashed lines and extending axially through the pedicle screw (102)) extends through the entire length of the pedicle screw (102). The channel (130) allows the pedicle screw (102) to be maneuvered over and receive a Kirschner wire, commonly referred to as a K-wire. The K-wire is typically pre-positioned using imaging techniques, for example, fluoroscopy imaging, and then used to provide precise placement of the pedicle screw (102). While the pedicle screw (102) illustrated in FIG. 3 includes a number of components, a number of variations may be made including, but in no way limited to, varying the type of driving feature (124), varying the shape and/or size of the head portion, varying materials, varying lengths, and the like.

Figure 4:
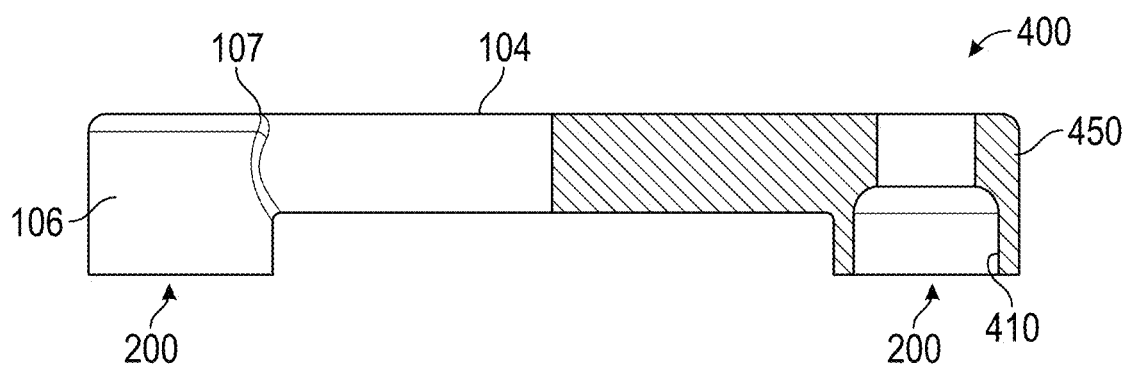
FIG. 4 is a side partial cut-away view of a tulip and rod assembly of the press-on pedicle screw system of FIG. 1, according to one exemplary embodiment.
Figure 5:
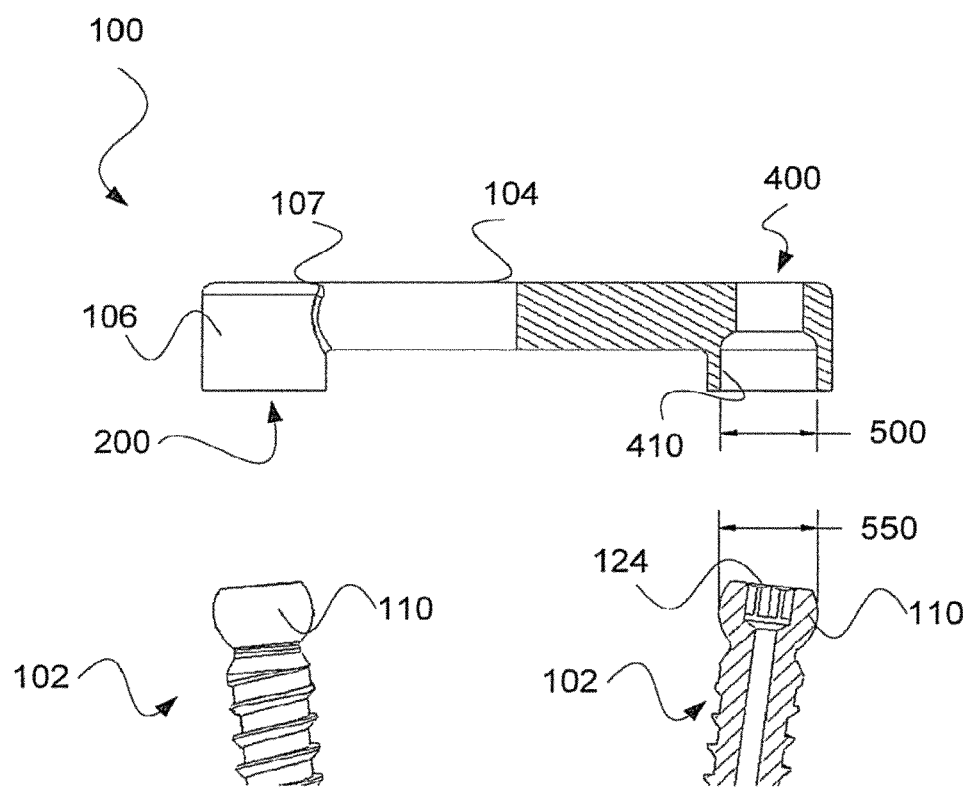
FIG. 5 is an exploded partial cut-away side view of the tulip assembly of FIG. 1, according to one exemplary embodiment.
Figure 6:
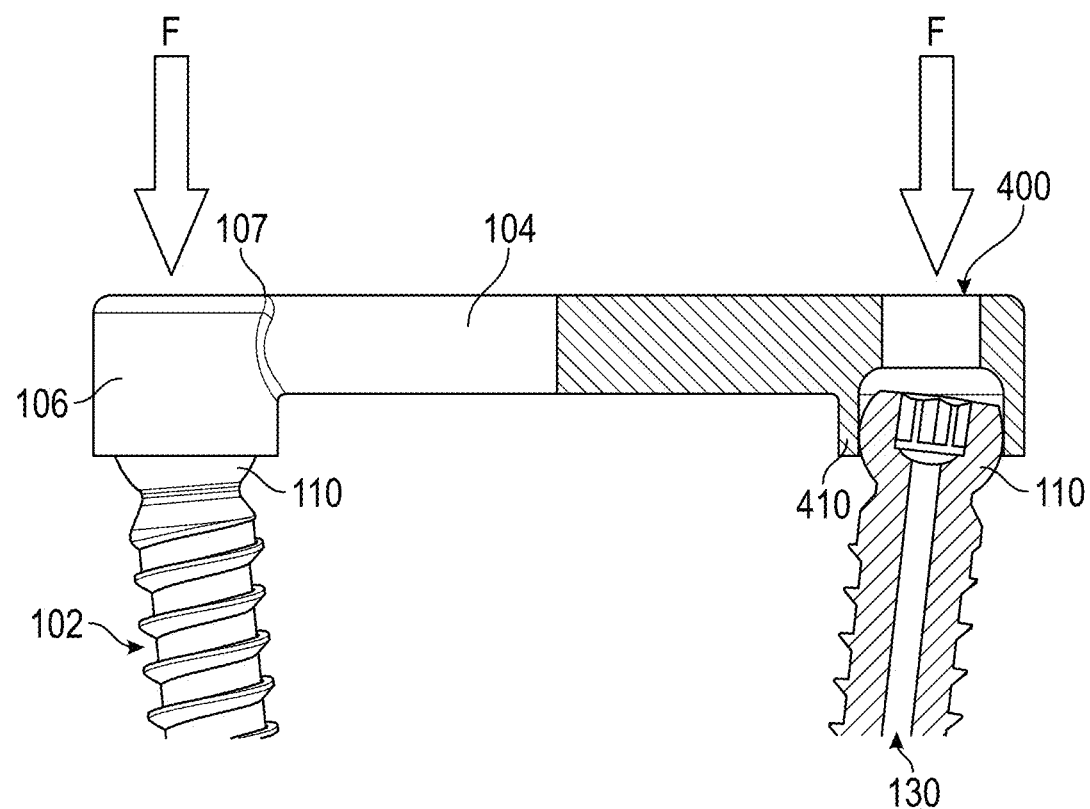
FIG. 6 is an assembled partial cut-away side view of the pedicle screw system of FIG. 1, according to one exemplary embodiment.

Returning again to FIG. 1, the pedicle screw system includes a tulip assembly (106) configured to be locked to the head portion (110) of a pedicle screw (102) via an interference fit. FIGS. 4, 5, and 6 illustrate the various components of the present exemplary tulip assembly (106), according to one exemplary embodiment. FIG. 4 illustrates a partially cut-away view of a tulip assembly (106), according to one exemplary embodiment. As illustrated in FIG. 4, the present exemplary tulip assembly (106) includes a generally cylindrical tulip body (450) defining an engagement orifice (200). As shown in FIG. 4, the engagement orifice (200) defined by the generally cylindrical tulip body (450) includes a screw head contact surface (410) forming an inner wall portion of the engagement orifice (200). According to one exemplary embodiment, when the present exemplary tulip assembly is coupled to the head portion (110) of a pedicle screw (102), the screw head contact surface (410) of the tulip assembly is sized to contact and securely couple the head portion of the pedicle screw via an interference fit.

Additionally, according to the exemplary embodiment illustrated in FIG. 4, an upper bore (400) is formed in the center of the tulip assembly (106) to provide access to and through the engagement orifice (200), thereby providing top access to a driving feature (124; FIG. 3) of a pedicle screw (102; FIG. 3) and/or a K-wire. While on exemplary engagement orifice (200) including an upper bore (400) is illustrated in FIG. 4, any number of geometries may be used to define the engagement orifice (200) according to the teachings of the present exemplary system and method.

FIG. 5 further illustrates an exemplary configuration for practicing the present exemplary system and method. As shown in FIG. 5, the present exemplary pedicle screw system (100) includes a rod member (104) permanently and securely coupled to a plurality of tulip assemblies (106). By permanently coupling the rod member (104) to the outer housing of the tulip assemblies (106), rod binding mechanisms are unnecessary in the formation of the tulip assemblies (106). Consequently, the outer diameter of the resulting pedicle screw system may be minimized, thereby reducing trauma and tissue damage to a patient. According to one exemplary embodiment, the rod member (104) may be coupled to the outer surface of the tulip assemblies (106) by any number of methods including, but in no way limited to, welding, forming the system from a single piece of material, adhesives, mechanical fasteners, and the like.

As mentioned previously, each of the tulip assemblies (106) includes an engagement orifice (200) including a screw head contact surface (410). According to one exemplary embodiment, the screw head contact surface (410) defines an internal diameter (500) of the tulip assembly (106). Additionally, as illustrated in FIG. 5, the screw head (110) of the exemplary pedicle screw (102) has a maximum screw head diameter (550). According to one exemplary embodiment of the present exemplary system and method, the internal diameter (500) defined by the screw head contact surface (410) is smaller than the maximum screw head diameter (550) of the screw head (110) of the exemplary pedicle screw (102), such that when the screw head of the exemplary pedicle screw (102) is pressed into the engagement orifice (200), the screw head and the screw head contact surface combine to create a press fit or an interference fit.

As used in the present specification, and in the appended claims, the term "interference fit" shall be interpreted broadly as including the joining of any two mating parts such that one or the other (or both) parts slightly deviate in size from their nominal dimension, thereby deforming each part slightly, each being compressed, the interface between two parts creating a union of extremely high friction. The word interference refers to the fact that one part slightly interferes with the space that the other is occupying in its nominal dimension.

According to one exemplary embodiment, the allowance, or planned difference from nominal size of both the internal diameter (500) defined by the screw head contact surface (410) is smaller than the maximum screw head diameter (550) of the screw head (110) is sufficiently large that the force sufficient to overcome the resulting interference fit between the screw head contact surface (410) and the screw head (110) is larger than a force sufficient to pull the screw (102) out of a bone, or approximately 200 inch pounds.

FIG. 6 illustrates the engagement of a tulip assembly (106) on a pedicle screw (102), according to one exemplary embodiment. As illustrated in FIG. 6, to engage the tulip assembly (106) to the screw head portion (110) of the pedicle screw (102), an instrument (not shown) can be coupled to the underside of the screw head (110) and to the top of the tulip assembly (106). Once positioned, a load (F) can be applied to the top of the tulip assembly (106) to press the screw head (110) into the engagement orifice (200). Similarly, disassembly can be achieved by pulling up on the tulip assembly (106) while driving an instrument through the upper bore (400) of the tulip assembly (106) to disengage the screw head (110) from the engagement orifice (200).

According to one exemplary embodiment, the desired interference fit sufficient to create a removal force of at least approximately 200 inch pounds may be dependent upon the materials used to form the screw head (110) and/or the screw head contact surface (410). Particularly, according to one exemplary embodiment, the screw head (110) and/or the screw head contact surface (410) is formed of one of a titanium, a cobalt chrome, and/or a nitinol (nickel titanium) based material. According to one exemplary embodiment, titanium, cobalt chrome, and/or nitinol, allow for a small amount of deformation without yielding. Consequently, as illustrated above, the difference in the maximum screw head diameter (550) of the screw head (110) and the internal diameter (500) defined by the screw head contact surface (410) is sufficient to provide an interference fit between the screw head and the screw head receptacle, without yielding the material of either component. Additionally, according to one exemplary embodiment, the interference fit is sufficiently strong to prevent the receptacle from being pulled off of the screw head, i.e., has a removal force of at least approximately 200 inch pounds.

Figure 7A:
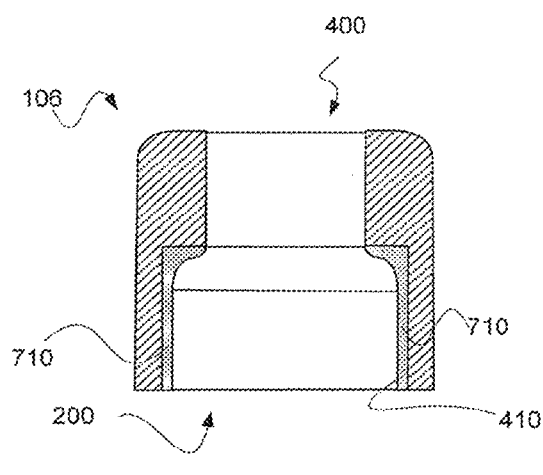
FIGS. 7A and 7B are cross-sectional side-views of a press-on tulip bodies, according to various exemplary embodiments.

According to one exemplary embodiment, the entire tulip assembly (106) may be formed of a known material such that the dimensions desired to create the interference fit can be readily calculated. Alternatively, as illustrated in FIG. 7A, one or more inserts (710) may be formed in the engagement orifice (200) to provide a screw head contact surface (410) with known properties, while not requiring that the remaining tulip assembly exhibit those same qualities. The placement of the one or more inserts (710) may be performed using any number of mechanical and/or chemical methods including, but in no way limited to, welding, using adhesives, material deposition methods, and the like.

While the interference fit provided above is described as occurring with only elastic deformation, the present system and method may be performed with slightly looser tolerances of the internal diameter (500) defined by the screw head contact surface (410) and the maximum screw head diameter (550) of the screw head (110) such that some plastic deformation occurs, so long as the removal force of the tulip assemblies (106) from the screw head (110) is sufficiently strong to prevent the receptacle from being pulled off of the screw head, i.e., has a removal force of at least approximately 200 inch pounds.

Furthermore, according to one exemplary embodiment, the surface defined by the screw head contact surface (410) has a constant diameter. Consequently, a single interference fit is achieved when engaged with the screw head (110). That is, according to one exemplary embodiment, the removal force will be substantially the same regardless of the level of engagement between the screw head contact surface (410) and the screw head (110).

Figure 7B:
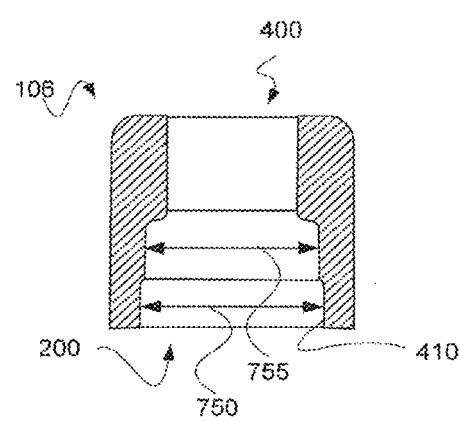
Figure 8:
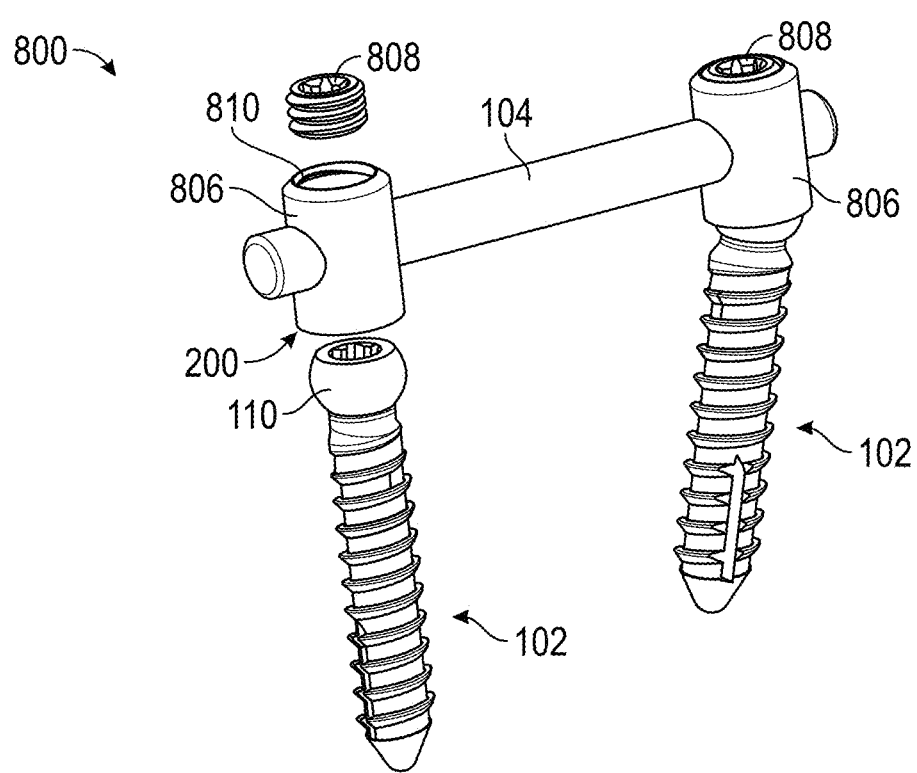
FIG. 8 is a partially exploded perspective view and of an alternative press-on pedicle screw system, according to one exemplary embodiment.
Figure 9:
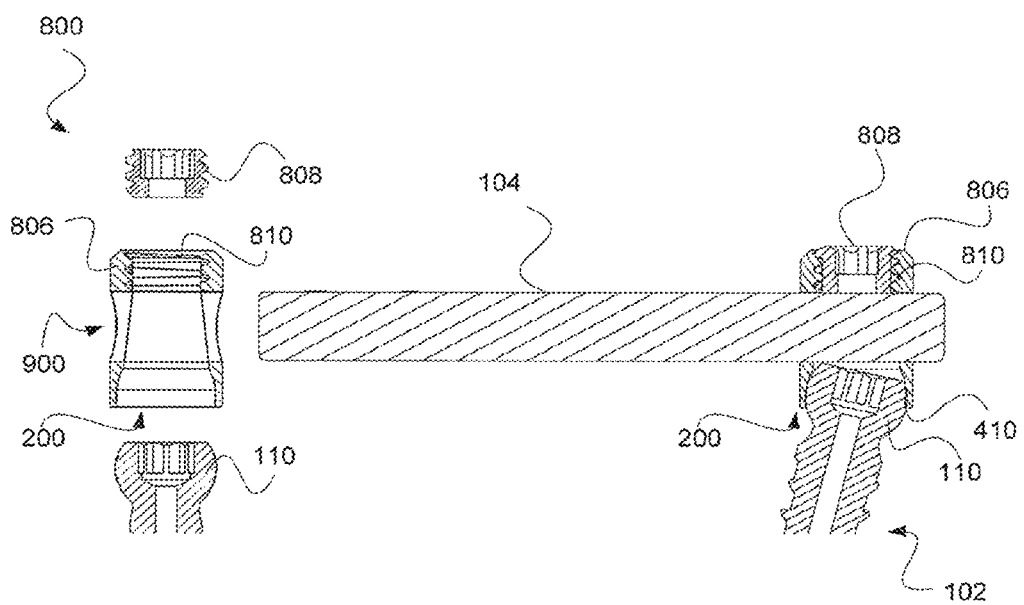
FIG. 9 is a cross-sectional partially exploded side view of the alternative press-on pedicle screw system of FIG. 8, according to one exemplary embodiment.

Alternatively, according to one exemplary embodiment illustrated in FIG. 7B, the internal diameter (500) defined by the screw head contact surface (410) may vary, providing a potential for differing levels of engagement between the screw head contact surface (410) and the screw head (110). Particularly, according to one exemplary embodiment, the tulip assembly (106) may have a first (750) and a second (755) internal diameter (500), both smaller than the maximum screw head diameter (550) of the screw head (110). According to this exemplary embodiment, a first larger diameter (750) may be engaged or press fit to the head (110) of the pedicle screw to form a provisional lock, thereby establishing the engagement of the tulip assembly while providing some resisted movement. Once a desired assembly and operation have been performed, the second smaller diameter (755) may be engaged with the maximum screw head diameter (550) of the screw head (110) to establish the final lock sufficient to maintain engagement.

While the above-mentioned exemplary embodiments are described as having the rod member (104) permanently coupled to the outer surface of the tulip assembly (106), thereby reducing the number of parts and the size of the pedicle screw system (100), any number of rod retention members may be formed in the upper portion of the tulip assembly to retain the rod member (104). According to one exemplary embodiment illustrated in FIGS. 8 and 9, an exemplary pedicle screw system (800) includes a tulip member (806), having an upper portion and a lower portion. According to the illustrated exemplary embodiment, the lower portion of the tulip member (806) includes an engagement orifice (200) to provide a screw head contact surface (410) as described above. However, in contrast to the tulip members described previously, the upper portion of the exemplary tulip member (806) illustrated in FIG. 8 includes a threaded inner wall (810) configured to receive a set screw member (808). Additionally, according to one exemplary embodiment, the exemplary tulip member (806) includes an orifice (900) passing through the walls of the exemplary tulip member (806). According to one exemplary embodiment, the orifice is sufficiently sized to allow for the reception and translation of the rod member (104) there through.

As the rod member (104) is passed through the orifice (900), the set screw (808) may be advanced along the threaded inner wall (810) of the exemplary tulip member (806) until it engages the rod member (104) and imparts a retaining force thereon.

Exemplary Implementation and Operation

Figure 10:
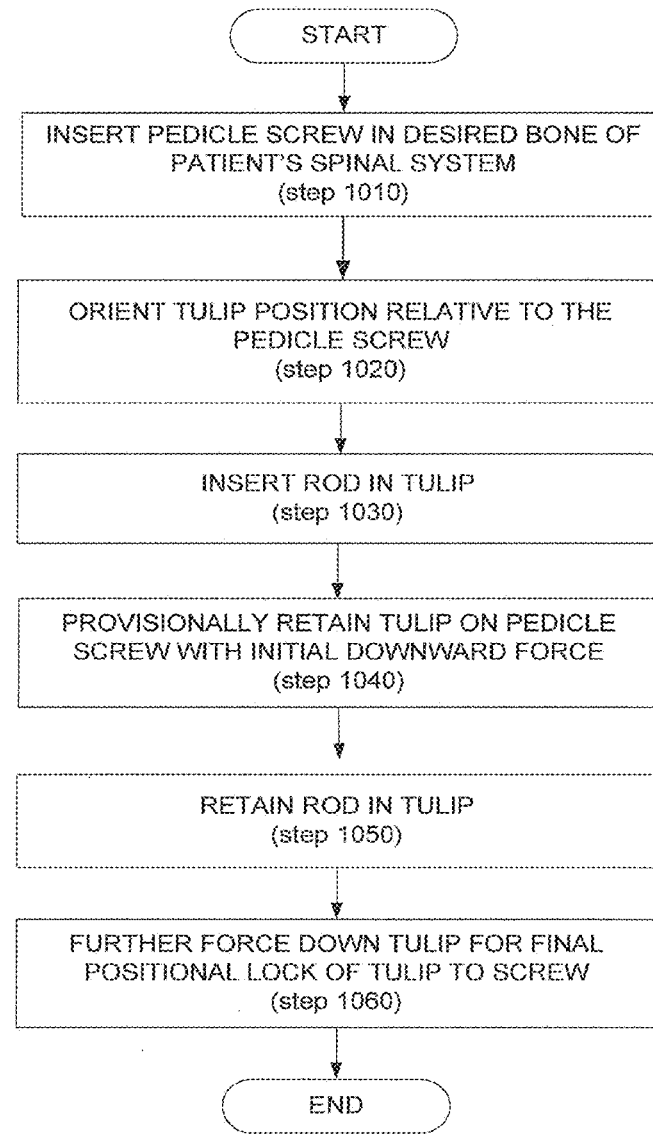
FIG. 10 is a flow chart illustrating a method for inserting a press-on tulip assembly on a pedicle screw, according to one exemplary embodiment.

FIG. 10 illustrates one exemplary method for utilizing the present exemplary press-on pedicle screw system, according to one exemplary embodiment. As illustrated in FIG. 10, the exemplary method may begin by first inserting screws into a desired bone of a patient's spine (step 1010). The placement and/or number of pedicle screw systems (100) to be used in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example. The pedicle screws (102) may be maneuverable to achieve a desired placement, orientation, and/or angular position.

Once the desired pedicle screw (102) is properly placed (step 1010), a tulip member (806) may be inserted and guided to the previously placed screw (step 1020). According to one exemplary embodiment, the placement of the tulip member (806) may be facilitated by the use of a Kirschner wire or non-invasive imaging methods including, but in no way limited to, x-ray imaging, magnetic resonance imaging (MRI), and/or fluoroscopy imaging, for example.

Once the tulip assembly (806) is at the desired position relative to the pedicle screw (102), the tulip assembly (806) can be fixed or locked onto the pedicle screw (102) by a downward force as described above. According to one exemplary embodiment, the tulip assembly (806) is fixed onto the pedicle screw (102), at least provisionally (step 1040), before the rod member (104) is inserted into the tulip assembly (802) (step 1030). In another embodiment, as illustrated in FIG. 10, the tulip assembly (806) is fixed onto the pedicle screw (102) contemporaneously as the rod is inserted into the tulip assembly (806), or even after the rod member (104) is inserted into the tulip assembly.

Once the tulip assembly (806) is provisionally retained on the screw (102), the rod (104) may be retained in the tulip assembly (806). According to one exemplary embodiment, the rod member (104) may be captured by the tulip assembly (806) by advancing the set screw (808) along the threaded inner wall (810) of the exemplary tulip member (806) until the set screw engages the rod member (104) and imparts a retaining force thereon. With the rod member (104) correctly positioned and any positional manipulation procedures completed, the tulip assembly (806) can be further advanced along the engagement orifice (200) to provide a final positional and angular lock of the tulip assembly relative to the screw (step 1060).

While the above-mentioned method is described and illustrated as a step-wise process, it will be understood that the illustrated order of performing the detailed steps is not necessary. Rather, the steps of the exemplary method illustrated herein may be performed in any number of combinations to practice the present exemplary system and method. Furthermore, a number of alternative embodiments may be formed using the present exemplary system and method. For example, according to one exemplary embodiment, the spherical shaped screw head (110) detailed above may be replaced with a cylindrical member having an engagement orifice (200). According to this exemplary embodiment, the rod connection member may be coupled to or include an integrally formed spherical member configured to be coupled to the engagement orifice (200) via an interference fit, as disclosed above. Additionally, according to various exemplary embodiments, the spherical member of the present system may include a dual-lobed member having a different diameter for each lobe, thereby allowing for provisional and final lock using a corresponding member having a single internal diameter.

As described previously, assemblies detailed herein have a smaller size envelope (e.g., less bulky, lower profile, and/or more compact shape) and are easier to place onto the pedicle screw than traditional designs. The smaller size and ease of installation may reduce trauma to the soft-tissue regions in the vicinity of the surgical site, which in turn generally allows for a quicker recovery by the patient. Yet another possible advantage of the present exemplary pedicle screw systems over existing systems is that all of the parts needed to lock the tulip assembly to the pedicle screw are included within the tulip assembly. Accordingly, once the tulip assembly is coupled to the pedicle screw, no additional member is needed to complete the assembly/installation of the pedicle screw system.

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the method and system be defined by the following claims.

What is claimed and desired to be secured by Letters Patent is:

1. An implant assembly comprising:
    a first pedicle screw comprising:
        a first pedicle screw head having a first pedicle screw head diameter; and
        a first pedicle screw elongate threaded portion coupled to and extending from the first pedicle screw head;
    a second pedicle screw comprising:
        a second pedicle screw head having a second pedicle screw head diameter; and
        a second pedicle screw elongate threaded portion coupled to and extending from the second pedicle screw head;
    a first tulip assembly having a first tulip assembly bore extending into the first tulip assembly, the first tulip assembly bore having a first tulip assembly bore first inner diameter defined by a first tulip assembly inner wall, the first tulip assembly bore first inner diameter being smaller than the first pedicle screw head diameter;
    a second tulip assembly having a second tulip assembly bore extending into the second tulip assembly, the second tulip assembly bore having a second tulip assembly bore first inner diameter defined by a second tulip assembly inner wall, the second tulip assembly bore first inner diameter being smaller than the second pedicle screw head diameter; and
    a rod connected to and extending between the first tulip assembly and the second tulip assembly.

2. The implant assembly of claim 1, wherein the first tulip assembly, the second tulip assembly, and the rod are coupled prior to coupling of the first tulip assembly to the first pedicle screw and the second tulip assembly to the second pedicle screw.

3. The implant assembly of claim 1, wherein the first tulip assembly, the second tulip assembly, and the rod are unitarily formed from a single piece of material.

4. The implant assembly of claim 1, wherein at least one of the first tulip assembly bore and the second tulip assembly bore is at least substantially cylindrical.

5. The implant assembly of claim 1, wherein the first tulip assembly bore permits head-first introduction of the first pedicle screw head into the first tulip assembly bore until a section having the first pedicle screw head diameter is within the first tulip assembly bore, thereby creating a compression fit between the first tulip assembly inner wall and the first pedicle screw head within the first tulip assembly bore due to the first pedicle screw head diameter being larger than the first tulip assembly bore first inner diameter.

6. The implant assembly of claim 5, wherein the compression fit is capable of withstanding at least 200 pounds of removal force between the first tulip assembly and the first pedicle screw along an axis of the first tulip assembly bore without relative movement of the first pedicle screw head along the first tulip assembly bore.

7. The implant assembly of claim 5, wherein the first tulip assembly is adapted to permit head-first introduction of the first pedicle screw head into the first tulip assembly bore to create the compression fit while at least a portion of the first pedicle screw elongate threaded portion is embedded in bone.

8. The implant assembly of claim 1, wherein the first pedicle screw head comprises a truncated spherical shape.

9. The implant assembly of claim 1, wherein the implant assembly comprises a material selected from at least one of a titanium alloy, a cobalt chrome alloy, and a nickel titanium alloy.

10. An implant assembly comprising:
    a pedicle screw comprising a head having a head diameter and an elongate threaded portion coupled to and extending from the head; and
    a tulip assembly comprising:
        a housing defining a bore comprising:
            an engagement orifice;
            a shape that is at least substantially fixed; and
            a first region inner diameter that is smaller than the head diameter of the pedicle screw;
        wherein head-first introduction of the head of the pedicle screw through the engagement orifice and into the bore creates a compression fit between the housing and the head of the pedicle screw due to the head diameter of the pedicle screw being larger than the first region inner diameter.

11. The implant assembly of claim 10, wherein the compression fit between the housing and the head of the pedicle screw is capable of withstanding at least 200 pounds of removal force between the tulip assembly and the pedicle screw along an axis of the bore without relative movement of the head of the pedicle screw along the bore.

12. The implant assembly of claim 10, wherein the bore comprises a second region having a second region inner diameter that is smaller than the first region inner diameter, wherein the second region is configured to receive a tool to disengage the pedicle screw from the tulip assembly.

13. The implant assembly of claim 10, wherein the engagement orifice is at least substantially circular and wherein an inner wall of the housing defines an at least substantially cylindrical portion of the bore extending into the housing from the engagement orifice.

14. The implant assembly of claim 10, wherein the head of the pedicle screw comprises a truncated spherical shape.

15. The implant assembly of claim 10, wherein the tulip assembly is connected to a rod, which in turn is coupled to an additional tulip assembly.

16. The implant assembly of claim 15, wherein the rod is coupled to the tulip assembly and the additional tulip assembly prior to implantation of the implant assembly by introduction of a pedicle screw into the bore of the tulip assembly.

17. The implant assembly of claim 10, wherein the housing comprises a material selected from at least one of a titanium alloy, a cobalt chrome alloy, and a nickel titanium alloy.

18. A method for affixing a press-on pedicle screw assembly to a spine, the method comprising:
inserting a first pedicle screw having a first pedicle screw head portion with a first pedicle screw head diameter into a first portion of a patient's spine;
inserting a second pedicle screw having a second pedicle screw head portion with a second pedicle screw head diameter into a second portion of the patient's spine;
obtaining a first tulip assembly having a first tulip housing defining a first tulip bore comprising:
a first tulip assembly engagement orifice;
a first tulip assembly shape that is at least substantially fixed; and
a first tulip assembly region inner diameter that is smaller than the first pedicle screw head diameter; and
applying a force between the first pedicle screw and the first tulip assembly whereby the first pedicle screw head portion is pressed into the first tulip bore, thereby creating a first compression fit between an inner wall of the first tulip housing and the first pedicle screw head portion.

19. The method as recited in claim 18, further comprising:
obtaining a second tulip assembly having a second tulip housing defining a second tulip bore comprising:
a second tulip assembly engagement orifice;
a second tulip assembly shape that is at least substantially fixed; and
a second tulip assembly region inner diameter that is smaller than the second pedicle screw head diameter; and
applying a force between the second pedicle screw and the second tulip assembly whereby the second pedicle screw head portion is pressed into the second tulip bore, thereby creating a second compression fit between an inner wall of the second tulip housing and the second pedicle screw head portion.

20. The method as recited in claim 19, further comprising connecting the first tulip assembly to the second tulip assembly via a rod before engaging the first tulip assembly to the first pedicle screw.

* * * * *